United States Patent
Beckmann

(10) Patent No.: US 6,908,536 B2
(45) Date of Patent: Jun. 21, 2005

(54) ELECTROCHEMICAL SENSOR

(75) Inventor: Udo Beckmann, Stockelsdorf (DE)

(73) Assignee: Drägerwerk Aktiengesellschaft, Lübeck (DE)

( * ) Notice: Subject to any disclaimer, the term of this patent is extended or adjusted under 35 U.S.C. 154(b) by 447 days.

(21) Appl. No.: 10/020,769

(22) Filed: Dec. 12, 2001

(65) Prior Publication Data

US 2002/0070128 A1 Jun. 13, 2002

(30) Foreign Application Priority Data

Dec. 13, 2000 (DE) .......................... 100 62 062

(51) Int. Cl.[7] .............................................. G01N 27/27
(52) U.S. Cl. ........................ 204/412; 204/406; 204/431; 422/82.01
(58) Field of Search ............... 204/406, 403.01–403.14, 204/411, 412, 416–418; 205/775, 777.5, 778, 789; 422/82.01–82.03; 324/444, 434, 436

(56) References Cited

U.S. PATENT DOCUMENTS

| 4,988,418 A | 1/1991 | Beck et al. ................ 205/780 |
| 5,282,950 A | * 2/1994 | Dietze et al. ................ 204/406 |
| 5,665,215 A | * 9/1997 | Bussmann et al. ........ 205/777.5 |
| 5,806,517 A | 9/1998 | Gerhardt et al. ............ 600/345 |
| 6,153,085 A | * 11/2000 | Patko et al. ................ 205/775 |

FOREIGN PATENT DOCUMENTS

| DE | 38 09 247 C2 | 10/1992 | ......... G01N/27/416 |
| DE | 197 24 888 A1 | 12/1998 | ......... G01N/27/403 |
| EP | 0 286 084 B1 | 7/1994 | ............ C12M/1/40 |
| EP | 0 333 246 B1 | 10/1994 | ........... G01N/27/00 |

* cited by examiner

*Primary Examiner*—Alex Noguerola
(74) *Attorney, Agent, or Firm*—McGlew and Tuttle, P.C.

(57) ABSTRACT

A digital electrochemical sensor is provided with a sensor electrode array (1–4) and an operating electronic unit integrated on a chip for processing electrical signals received therefrom. The operating electronic unit includes a potentiostat circuit and a microprocessor, which receives and further processes the signals processed by the operating electronic unit. To provide an electrochemical sensor which can be operated more simply and with higher precision during installation and in operation the potentiostat circuit is a digital circuit, whose controller function is controlled by the microprocessor (20), and for the microprocessor (20) to be also integrated on the chip of the operating electronic unit.

6 Claims, 4 Drawing Sheets

ELECTROCHEMICAL SENSOR

FIELD OF THE INVENTION

The present invention pertains to an electrochemical sensor with a sensor electrode array, an operating electronic unit integrated on a chip for operating the sensor electrode array and for processing the electrical signals received by it, wherein the operating electronic unit includes a potentiostat circuit, and with a microprocessor, which receives and further processes the signals processed by the operating electronic unit.

BACKGROUND OF THE INVENTION

Electrochemical sensors are frequently used in occupational safety, medical engineering, process measuring engineering, environmental analysis, etc. Such sensors have electrode arrays with two, three or more electrodes, which are called auxiliary electrode. reference electrode, and working electrode(s). The reference electrode is eliminated in the two-electrode sensor, and the auxiliary electrode is called the counterelectrode. A so-called potentiostat is needed to operate these sensors. This potentiostat regulates the potential difference between the reference electrode and the working electrode(s) to a preset value. The measured signal, which depends on the substance concentration to be measured, is derived from the current of the working electrode(s). Thus, the potentiostat also has the function of measuring the current in these working electrodes.

An electrochemical sensor of the type mentioned in the introduction has been known from DE 197 24 888 A1, in which an electrochemical gas sensor is described, which has a sensor electrode array, which is connected to an operating electronic unit, which is integrated on a chip, and the operating electronic unit communicates with a separate microprocessor which is remote from the sensor proper. A potentiostat circuit, which includes an analog control circuit, is also accommodated on the chip in this prior-art sensor. A typical analog potentiostat circuit is shown in FIG. 3 of the present application. Such potentiostat circuits tend in some sensors to hunt or do not regulate the potential difference between the working electrode and the reference electrode with an optimal time response. Furthermore, sensor aging effects may cause the regulation to become unstable. This is due to the fact that the control parameters are determined by the dimensioning of the electric circuit components, as they are shown, e.g., in FIG. 3. Therefore, changes can be made in the fixed controller parameters defined by such circuits only by making hardware changes on the electronic circuit components, which implies practically such a considerable effort that such changes are not practical.

A general problem of many electrochemical sensors is that the highly sensitive electrode arrays often deliver only very weak signals with measured currents on the order of magnitude of a few nanoA. The problem of very weak electrical sensor signals will become even more acute in the future due to the low limit values specified in many areas of application, to which a sensor is to respond with a high level of reliability, because the limit values of the variables to be measured will be lowered rather than raised in many areas due to strict specifications. The evaluation of electrical sensor signals with measured currents in the nanoA range requires highly sensitive electric circuits for processing and further processing, which are inherently also susceptible to the effect of electromagnetic disturbances because of their high sensitivity. This problem is tackled in the sensor of the type mentioned in the introduction by integrating all circuits of the operating electronic unit on one chip, so that only digital signals must be transmitted from the chip to the microprocessor and vice versa, the digital communication with the microprocessor having a low fault liability. Nevertheless, the measured signal that is taken off from the potentiostat circuit is an analog signal, which is subsequently passed on to the next circuits of the operating electronic unit for further processing, and is susceptible to fault at this first stage.

An electronic memory (an electronically erasable programable read only memory—EEPROM) is frequently integrated in more recent sensors in order to store sensor data, such as the type of the sensor, potentials, calibration coefficients, etc. and to make them available to the operating electronic unit.

To monitor a larger area, e.g., on the premises of a plant, a plurality of measuring heads with a sensor each are placed in a distributed pattern. An operating electronic unit of its own, which is accommodated in the measuring head together with the sensor electrode array, is thus, of course, also needed for each sensor. The transmission of the measured values and the power supply to the measuring heads are carried out by means of a star-shaped network to and from a central point. A plurality of measuring heads must be installed and operated in such systems, which implies a great installation and maintenance effort in light of the fact that, as was described above, sensor aging effects or other changes may occur in individual sensors and require corresponding corrections.

SUMMARY AND OBJECTS OF THE INVENTION

The object of the present invention is therefore to provide an electrochemical sensor which can be operated in a simpler manner and with higher precision at the time of the installation and during operation.

An electrochemical sensor according to the invention includes a sensor electrode array, an operating electronic unit integrated on a chip for operating the sensor electrode array and for processing electrical signals received therefrom. The operating electronic unit includes a potentiostat circuit with a microprocessor, which receives and further processes the signals processed by the operating electronic unit. The potentiostat circuit is designed as a digital control circuit, whose controller function is controlled by the microprocessor. The microprocessor is also integrated on the chip of the operating electronic unit.

Circuits that are controlled digitally by a processor for performing a controller function have been known per se in other fields of application. Therefore, digital controllers will not be described in detail here.

The use of a digital controller for the potentiostat circuit would not have been considered in the case of prior-art sensors of the type described in the introduction because the external microprocessor, which is part of the digital controller, would lead to relatively great disturbances in the highly sensitive measured signals because of its distance from the operating electronic unit.

The combination according to the present invention, namely, the fact that the potentiostat circuit is designed as a digital controller circuit, on the one hand, and the integration of the microprocessor on the chip of the operating electronic unit, on the other hand, makes it possible to embody the digital potentiostat circuit without this leading to a disturbing impairment of the sensitive measured signals. The use of a digital potentiostat circuit offers various advantages. It is possible as a result for the microprocessor controlling the controller function to adapt itself with its control algorithm to changes, e.g., to changes caused by aging processes in the sensors, so that an optimally adapting controller function can always be obtained. Furthermore. it is possible for the microprocessor to read data pertaining to the sensor, e.g., the type of the sensor, the operating potentials, calibration constants. etc., which can also be entered as input parameters into the control algorithm of the digital potentiostat circuit, from a likewise available read-only memory, which makes possible a direct adaptation of the controller function to the particular sensor.

Furthermore, a further miniaturization of the sensor measuring heads becomes possible due to the present invention, because the microprocessor is no longer provided as an external component.

Furthermore, the installation effort can be reduced in systems with a plurality of measuring heads, because a digital interface can be designed as a bus system, which is especially advantageous in distributed systems with a plurality of measuring heads.

Thus, an electronic memory, a microcomputer, a digital interface, a multiplexer, an analog/digital converter, and a digital/analog converter can be integrated on the chip of the electrochemical sensor. No additional analog electronic circuits are needed for the potentiostat circuit.

The space requirement and the manufacturing costs of the sensor are reduced by this reduction in the number of components and their compact arrangement on one chip. Thus, more favorable monitoring of small areas, e.g., in process plants, also becomes possible, or the monitoring of such areas now becomes possible for the first time ever.

Due to the integrated arrangement of these components, especially the microprocessor and digital potentiostat circuit components, it now becomes possible for the first time ever to design the potentiostat circuit as a digital circuit, i.e., to embody a digital controller. The potential difference between the working electrodes and the reference electrode is obtained at a preset value in case of a suitable control algorithm, which is implemented in the microprocessor. The control parameters for the digital potentiostat circuit can be kept ready in an electronic memory. An alternative embodiment makes provisions for the control algorithm to be designed such that the control parameters are acquired and set automatically when the sensor is put into operation. It is particularly advantageous to adapt the control parameters by measuring the sensor parameters. This may also be repeated at preset fixed intervals or triggered by a certain event.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 3:
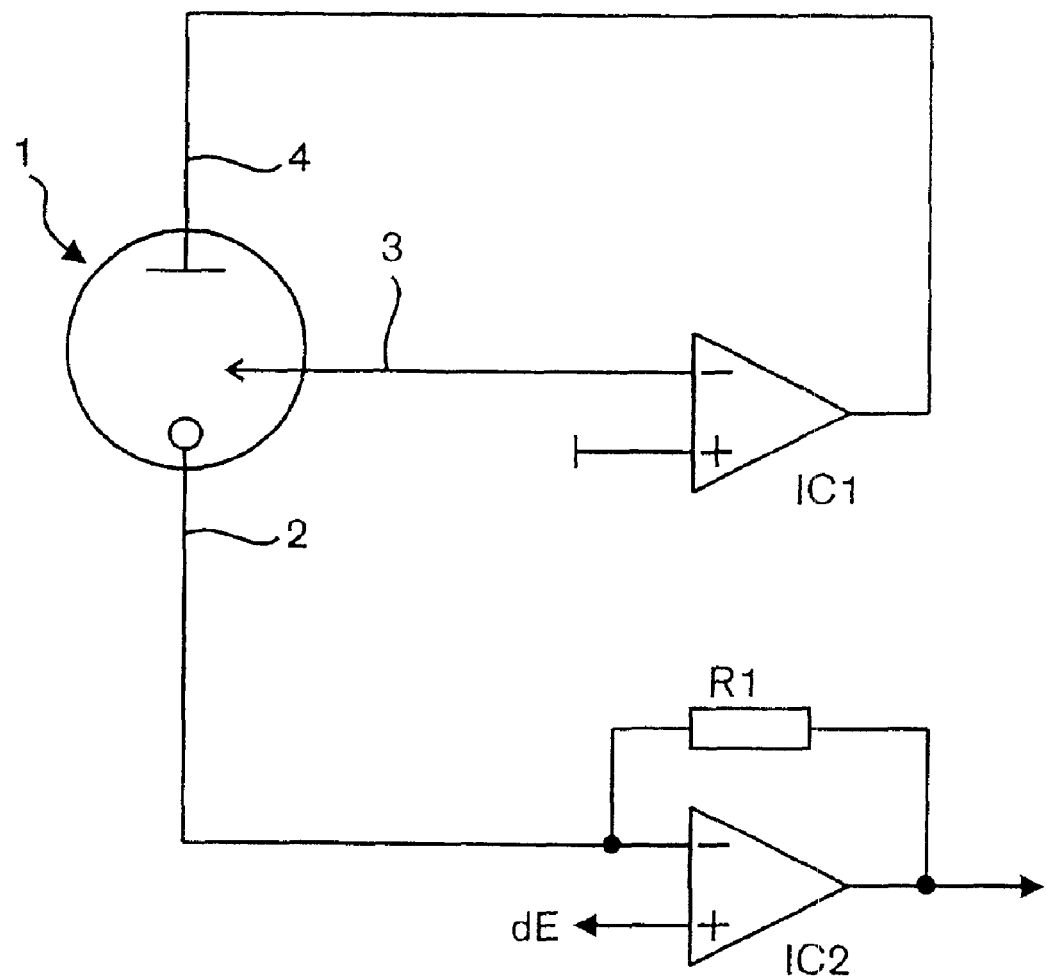
FIG. 3 is a general layout of an analog potentiostat circuit for a three-electrode sensor corresponding to the state of the art.
Figure 4:
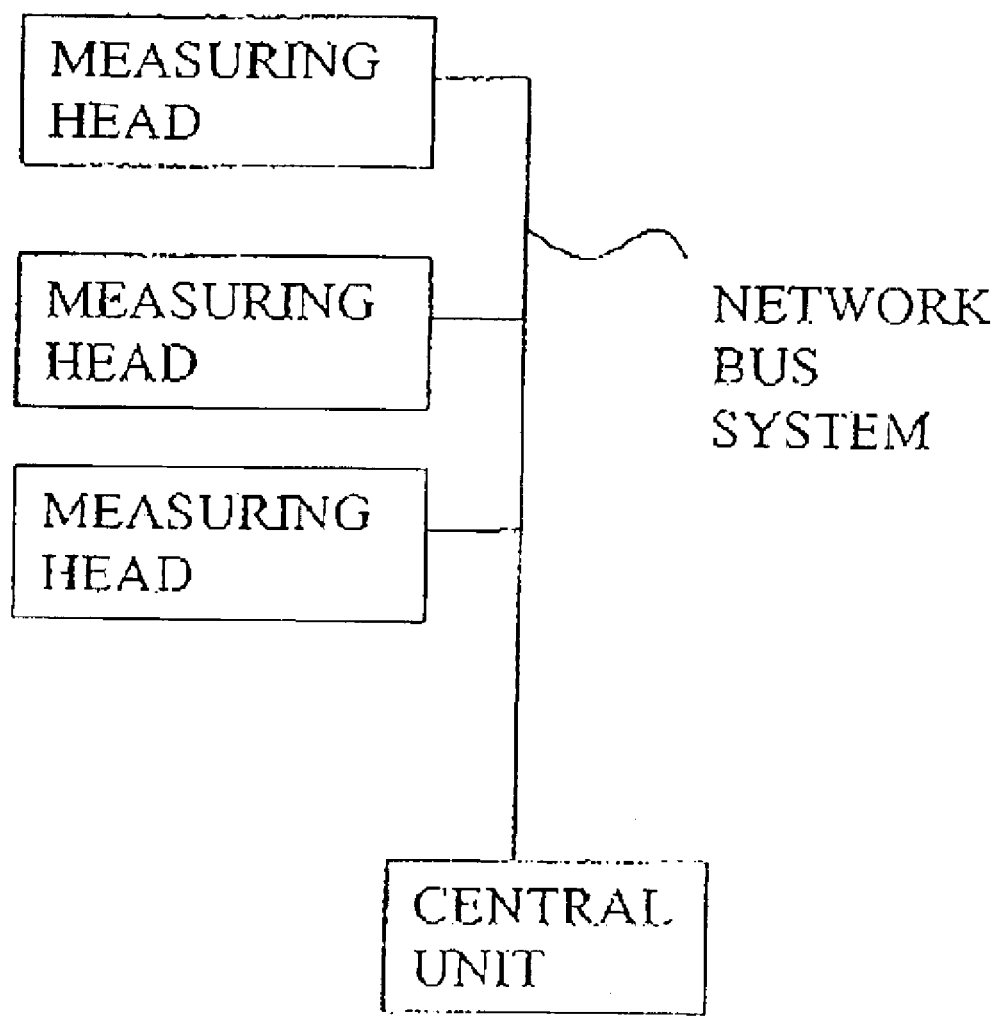
FIG. 4 is a schematic view of the present invention showing a plurality of measuring heads connected by a network bus system to a central unit.

Referring to the drawings in particular, FIG. 3 shows the basic circuit diagram of an analog potentiostat circuit for a three-electrode sensor corresponding to the state of the art. The electrode array of the sensor has a working electrode 2, a reference electrode 3, and an auxiliary electrode 4. As can be seen, operational amplifiers are used here to build up the control circuit for setting the voltage difference and to read out the measured signal, which is thus outputted as an analog signal.

Figure 1:
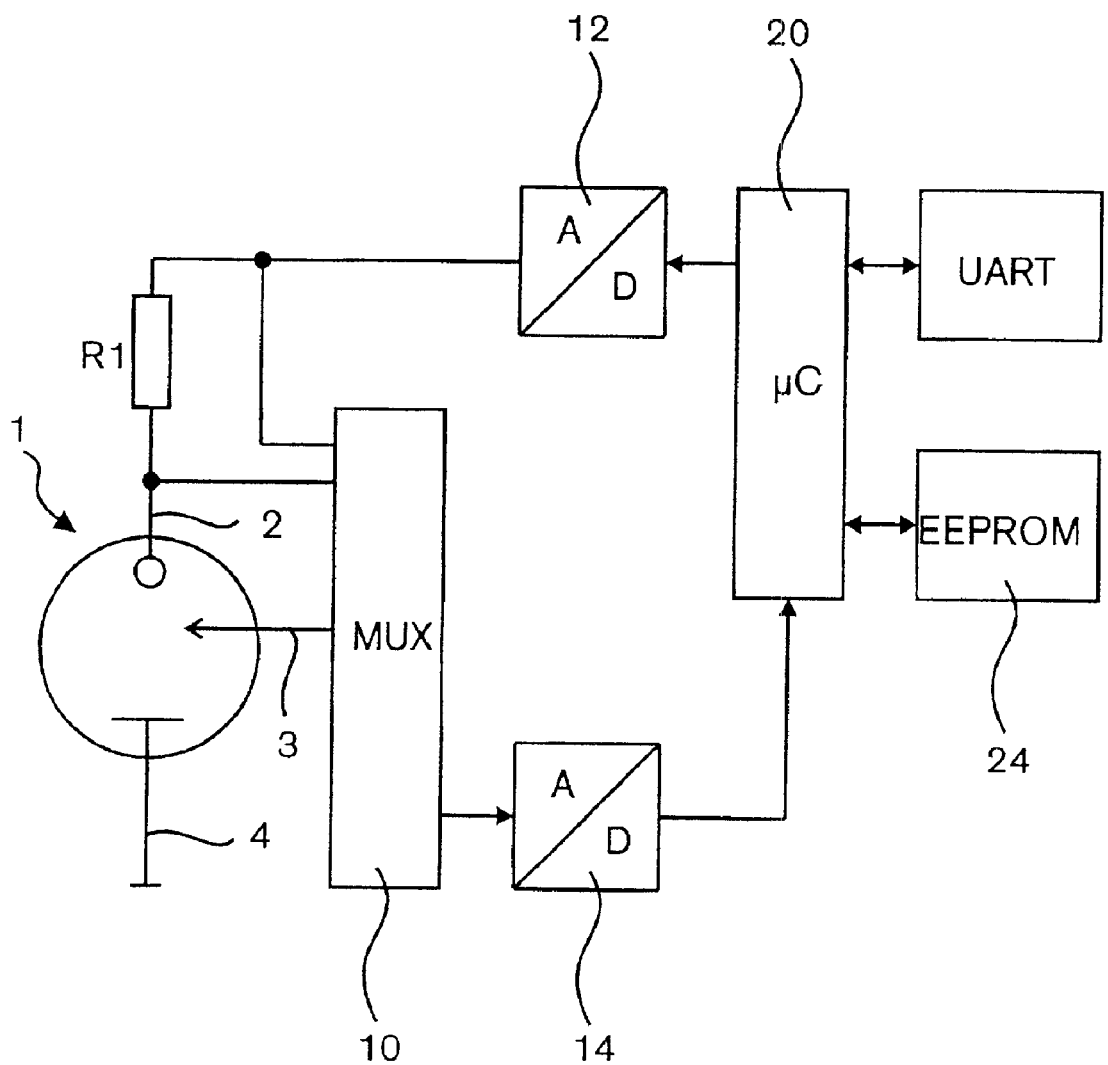
FIG. 1 is a schematic block diagram of a digital electrochemical sensor.

In contrast, FIG. 1 shows the block diagram of a sensor in which the microprocessor is integrated within the operating electronic unit and the potentiostat circuit is designed as a digital control circuit. The sensor electrode array 1 with the working electrode 2, the reference electrode 3 and the auxiliary electrode 4 is joined by a multiplexer 10, which passes on the measured signals via an analog/digital converter 14 to a microprocessor 20. Furthermore, the microprocessor 20 is connected to a digital/analog converter 12, which generates an analog signal corresponding to the digital signal sent by the microprocessor 20, which is used to control the potential difference on the sensor electrode array 1. The control algorithm taking place in the microprocessor 20 embodies here, together with the converter circuits 12, 14 and the multiplexer circuit 10, a digital controller, which forms the potentiostat circuit. Furthermore, an electronic memory 24 is provided, in which, e.g., the operating parameters of the sensor electrode array can be stored, these operating parameters being read in by the microprocessor 20 in order to adapt the control algorithm to them.

Figure 2:
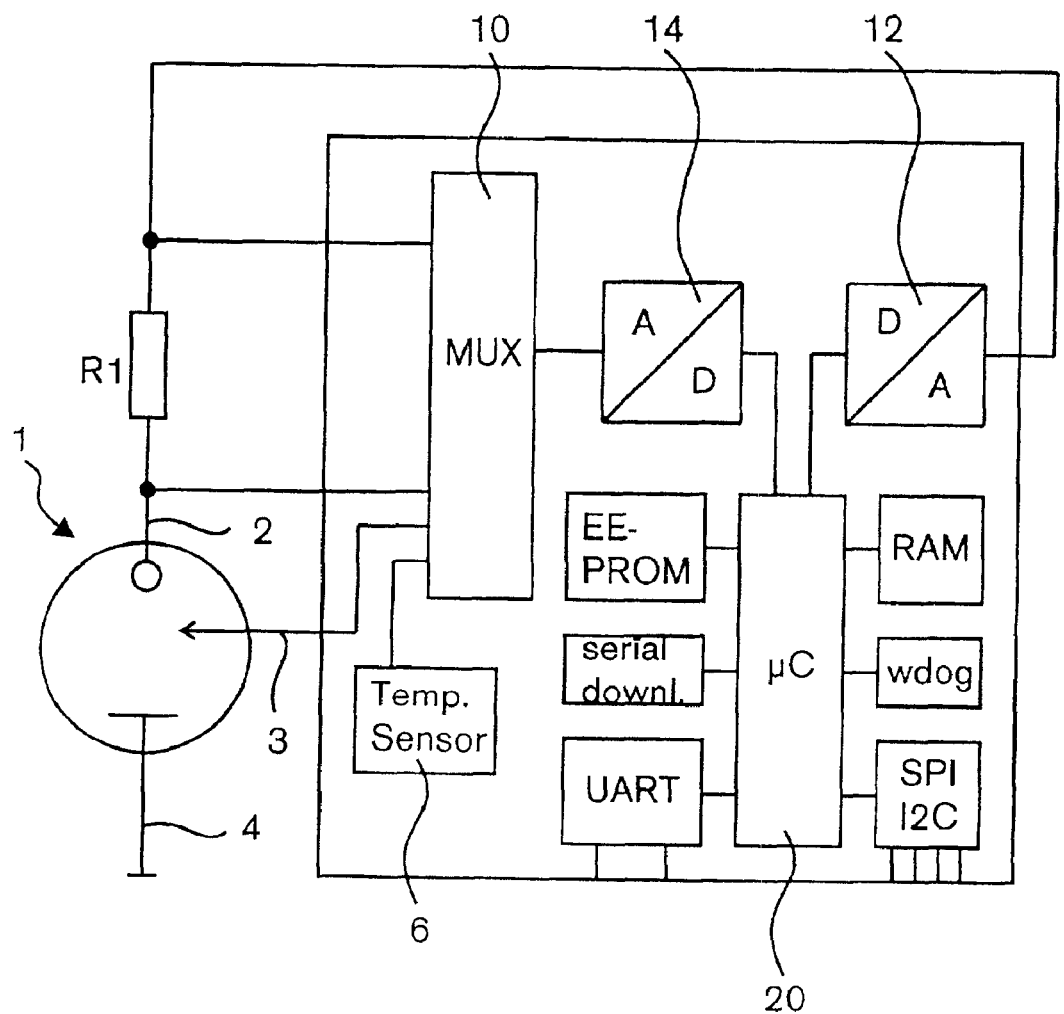
FIG. 2 is a more detailed embodiment of the operating electronic unit and microprocessor as a block diagram.

FIG. 2 shows a more detailed view of the circuit components of the operating electronic unit and the microprocessor. The central component of the microprocessor 20 is formed by a microcontroller, which receives the converter measured signals from the analog/digital converter 14, which in turn receives the signals of the sensor electrode array 1 as well as those of a temperature sensor 6 via the multiplexer 10. The temperature sensor 6 may replace the NTC resistor needed otherwise for the temperature compensation of the sensor characteristic. Furthermore, a digital/analog converter 12 is integrated on the chip; this converter 12 converts the digital control signals of the microprocessor 20 into analog control signals for the control of the potential difference on the sensor electrode array 1 and thus embodies the control function of the digital potentiostat circuit, which control function is preset by the control algorithm taking place in the microprocessor 20.

If the digital interface of the circuit shown in FIG. 2 is designed as an Ethernet interface, complete control and monitoring of the digital electrochemical sensor within the entire company or worldwide is possible via the Intranet or Internet. The power supply for the sensor may also be taken from the Ethernet connection.

The individual electrochemical sensors can be made very compact with the design described, because the entire operating and evaluating electronic unit is accommodated in an extremely compact manner on one chip, which is connected to a central unit via a digital interface. Furthermore, each sensor can respond to changes flexibly, because the control function of the potentiostat circuit is not predetermined by the hardware design of a circuit, as in analog potentiostat circuits, but by the control signals generated by the control algorithm in the microprocessor, and the control algorithm can be designed to be so flexible that the control function adapts itself to changed environmental conditions. aging-related changes in the sensor electrode array and the like.

While specific embodiments of the invention have been shown and described in detail to illustrate the application of the principles of the invention, it will be understood that the invention may be embodied otherwise without departing from such principles.

What is claimed is:

1. An electrochemical sensor arrangement comprising:
    a plurality of measuring beads arranged at spaced locations from each other, each of said measuring heads includes a sensor electrode array, and an operating electronic unit with an analog to digital converter connected to said array, each said operating unit also including a digital to analog converter connected to said array, and a microprocessor connected to said analog to digital converter and to said digital to analog converter, said microprocessor processing signals from said array with a control algorithm to measure substance concentration at said array, said control algorithm operating said analog to digital converter and said digital to analog converter to form a potentiostat, said microprocessor, said analog to digital converter and said digital to analog converter being integrated on a single chip, each of said measuring heads including a digital network interface connected to said microprocessor;
    a network bus system connected to said network interface of said measuring heads;
    a central unit connected to said network bus system for repetitively monitoring said plurality of measuring heads.

2. A sensor arrangement in accordance with claim 1, wherein:
    said network bus system is an Ethernet network.

3. A sensor arrangement in accordance with claim 2 wherein:
    a power supply for said operating electronic unit is taken from said network interface;
    said network bus system is one of the Internet or an Intranet;
    said each measuring head includes a memory storing parameters of a respective said measuring head, said control algorithm of a respective said measuring head using said parameters to operate, a respective said microprocessor repetitively measures and updates said parameters, and stores said parameters in said memory.

4. A sensor arrangement in accordance with claim 1 wherein:
    a power supply for said operating electronic unit is taken from said network interface.

5. A sensor arrangement in accordance with claim 1 wherein:
    said network bus system is one of the Internet or an Intranet.

6. A sensor arrangement in accordance with claim 1, wherein:
    said each measuring head includes a memory storing parameters of a respective said measuring head, said control algorithm of a respective said measuring head using said parameters to operate the operating unit, a respective said microprocessor repetitively measures and updates said parameters, and stores said parameters in said memory.

* * * * *